(12) United States Patent
Zhang et al.

(10) Patent No.: US 10,597,678 B2
(45) Date of Patent: Mar. 24, 2020

(54) BIS-ALKOXYL AMIDE ALKYL CATIONIC PEPTIDE LIPIDS, SYNTHESIS METHOD THEREOF, AND APPLICATION THEREOF

(71) Applicant: DALIAN NATIONALITIES UNIVERSITY, Dalian, Liaoning (CN)

(72) Inventors: Shubiao Zhang, Liaoning (CN); Yinan Zhao, Liaoning (CN); Shaohui Cui, Liaoning (CN); Huiying Chen, Liaoning (CN); Quan Zhou, Liaoning (CN)

(73) Assignee: DALIAN NATIONALITIES UNIVERSITY, Dalian (CN)

( * ) Notice: Subject to any disclaimer, the term of this patent is extended or adjusted under 35 U.S.C. 154(b) by 0 days.

(21) Appl. No.: 15/550,472

(22) PCT Filed: Jun. 25, 2015

(86) PCT No.: PCT/CN2015/082260
§ 371 (c)(1),
(2) Date: Aug. 11, 2017

(87) PCT Pub. No.: WO2016/192149
PCT Pub. Date: Dec. 8, 2016

(65) Prior Publication Data
US 2018/0051302 A1    Feb. 22, 2018

(30) Foreign Application Priority Data

Jun. 4, 2015 (CN) .......................... 2015 1 0305970

(51) Int. Cl.

| | | |
|---|---|---|
| C12N 15/88 | (2006.01) | |
| A61K 9/127 | (2006.01) | |
| C07K 1/06 | (2006.01) | |
| C07K 5/09 | (2006.01) | |
| C07K 5/11 | (2006.01) | |
| A61K 47/54 | (2017.01) | |
| C07K 5/068 | (2006.01) | |
| C07K 4/00 | (2006.01) | |

(52) U.S. Cl.
CPC ............ *C12N 15/88* (2013.01); *A61K 9/1272* (2013.01); *A61K 47/542* (2017.08); *C07K 1/06* (2013.01); *C07K 1/066* (2013.01); *C07K 4/00* (2013.01); *C07K 5/06086* (2013.01); *C07K 5/0815* (2013.01); *C07K 5/1019* (2013.01)

(58) Field of Classification Search
None
See application file for complete search history.

(56) References Cited

U.S. PATENT DOCUMENTS

2002/0007073 A1*   1/2002  Schneider ............ A61K 9/1272
548/339.1

FOREIGN PATENT DOCUMENTS

| CN | 102006890 | 4/2011 |
|---|---|---|
| CN | 103613516 | 3/2014 |
| WO | WO9601840 | 1/1996 |

OTHER PUBLICATIONS

Zhao et al., Novel gemini cationic lipids with carbamate groups for gene delivery. J Mater Chem B Mater Biol Med. May 21, 2014; 2(19): 2920-2928 (Year: 2014).*
McGregor et al., Rational Approaches to the Design of Cationic Gemini Surfactants for Gene Delivery. J. Am. Chem. Soc., vol. 123, No. 26, 2001, pp. 6215-6220. (Year: 2001).*
International search report dated Feb. 26, 2016 from corresponding application No. PCT/CN2015/082260.
Zhao, Yinan et al., "Tri-peptide cationic lipids for gene delivery", Journal of Materials Chemistry B, No. 3, Sep. 30, 2014 (Sep. 30, 2014), pp. 119-126.

\* cited by examiner

*Primary Examiner* — Christopher M Babic
*Assistant Examiner* — Arthur S Leonard
(74) *Attorney, Agent, or Firm* — Hauptman Ham, LLP

(57) ABSTRACT

A bis-alkoxyl amide alkyl cationic peptide lipid has a chemical structure as below:

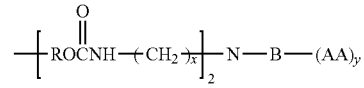

wherein the bis-alkoxyl amide alkyl cationic peptide lipid is dispersed in water to obtain the cationic peptide liposome which are high in stability and uniform in dispersion and have about 120 nm of average grain diameter and Zeta electric potential between 30 and 50 mV. The liposome can effectively compress the plasmids DNA and siRNA, can efficient transfection both in-vitro and in-vivo, and almost does not have toxicity to cells and mice, so that the liposome can be widely applied in gene delivery as a gene vector.

7 Claims, 6 Drawing Sheets

BIS-ALKOXYL AMIDE ALKYL CATIONIC PEPTIDE LIPIDS, SYNTHESIS METHOD THEREOF, AND APPLICATION THEREOF

RELATED APPLICATIONS

The present application is a National Phase of International Application Number PCT/CN2015/082260, filed Jun. 25, 2015, and claims the priority of China Application No. 201510305970.7, filed Jun. 4, 2015.

FIELD OF THE INVENTION

The invention relates to the biotechnological field, and more particularly relates to non-viral genetic vectors and preparation method thereof.

BACKGROUND OF THE INVENTION

With the constantly deepening recognition on the pathogenesis of diseases in the cell level, gene therapy has become the study focus of scientists. For gene therapy, exogenous gene DNA or RNA fragments are introduced into target cells or tissues to correct or make up for the defects of genes, close or inhibit the expressions of abnormal genes, and thereby fulfilling the aim of treating diseases. Gene therapy, as a new treatment means, can treat multiple diseases, including cancers, hereditary diseases, infectious diseases, cardiovascular diseases and autoimmune diseases, in which the gene therapy for cancers is the main application field. The vectors for gene delivery mainly comprise viral vectors and non-viral vectors. The viral vectors, such as recombinant adenovirus vectors, are very effective in transfection efficiency and can target most of cells, and thereby getting certain superiority in the gene delivery. However, it will cause in-vivo immunoreaction and contains transcriptional virus gene, which may cause genetic recombination or complement in vivo to further harm human bodies. Compared with the viral vectors, the non-viral vectors are limited in transfection efficiency, but have the advantages of no infectiousness, no limits to vector capacity, controllability in chemical structure, easy preparation in large quantities and so on, hence, more and more people have been increasingly appreciating the non-viral vectors.

Cationic liposomes have the cell-like structure and the characteristic of a biological membrane and they can be degraded in vivo, cationic liposomes can protect the biological activity of the fragment of their carried genes, which have become non-viral gene transfection vectors with the clinical potential. Under the structure of the liposome, genes can be compressed to form complexes, and the complexes are delivered to lesion tissues or cells. Since 1987, after Felgner, et al. carried out transfection successfully on cells, such as COS-7 by utilizing N-[1-(2,3-dioleoacyloxy)propyl]-N,N,N-trimethyl ammonium chloride (DOTMA) for the first time, the liposome has developed to the most popular gene transfer means except for the retrovirus vectors, and particularly, is mainly applied in the treatment of tumors, cystic fibrosis and other diseases. Because there are some limitations for the liposome, such as high cytotoxicity and non-obvious targeting on organs and undefined gene delivery mechanism, the liposome cannot be widely applied. Hence, people have devoted themselves to various constructions and chemical modifications of the cationic liposome, trying to seek a gene therapeutic drug with high efficiency and low toxicity.

The liposome has developed for nearly 30 years, which has formed the perfect liposome vector systems from widely used quaternary ammonium salt head and guanidine group head to polyamine head cationic lipid, however, there are many problems for these vector systems, for example, the transfection efficiency of mediated genes needing be improved; no directional recognition on target tissues; after the cationic liposome/DNA complex entering into cells, nucleic acid being constrained in endosome and difficult to release, which is adverse to its expression in cytoplasm or cell nucleus, so it cannot achieve the purpose of treatment. The Chinese patent application CN103613516A, 2014 Mar. 5 discloses a preparation method for Gemini cationic lipids and use thereof in drugs or gene delivery, the vector has certain cytotoxicity due to its poor biodegradability with the double head structure, resulting in restrictions to the aspect of in-vivo gene transfection.

SUMMARY OF THE INVENTION

The invention aims to provide a bis-alkoxyl amide alkyl cationic peptide lipid with little cytotoxicity and high in-vivo and in-vitro gene transfection efficiency and synthetic method and uses thereof.

The technical solution of the invention comprises:

I. A bis-alkoxyl amide alkyl cationic peptide lipid and preparation method thereof 1. A bis-alkoxyl amide alkyl cationic peptide lipid having a chemical structure expressed by a general formula I:

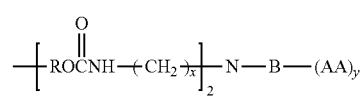

I wherein,
x is selected from 1 to 6, most preferably 2 to 4;
y is selected from 1 to 8, most preferably 2 to 4;
R is selected from $C_{8-20}$ alkyl, and the alkyl comprises straight-chain alkyl and branched chain alkyl;
AA is selected from arginine (Arg), histidine (His), aspartic acid (Asp), alanine (Ala), glycine (Gly), ornithine (Orn) or lysine (Lys);
B is selected from ornithine (Orn) or lysine (Lys).

2. A synthetic method for the bis-alkoxyl amide alkyl cationic peptide lipid comprise the following steps of: preparing a peptide head intermediate using amino-protected amino acid; carrying out acylation by an acylation reagent and an alcohol compound, and reacting the acylated product with polyamine compounds to prepare a dual long-carbon chain intermediate; linking the prepared peptide head intermediate with the prepared dual long-carbon chain intermediate via amidation; and removing protecting groups to react with amino-protected amino acid, and after the deprotection obtaining the bis-alkoxyl amide alkylated cationic peptide lipid compound.

The specific steps are as follows:

(1) carrying out acylation via an acylation reagent and an alcohol compound, wherein the acylation reagent is carbonyl diimidazole, and the alcohol compound isdodecanol, tetradecanol, hexadecanolor octadecanol, the molar ratio of the acylation reagent to the alcohol compound is 1:10 to 10:1, the reaction solvent is toluene, dichloromethane, DMF or chloroform, the reaction temperature is 10° C. to 60° C., and the reaction time is 0.5 h to 12 h;

(2) reacting the acylated product with a polyamine compound to prepare a dual long-carbon chain intermediate. The polyamine compound is polyamine selected from diethylenetriamine, dipropylenetriamine or dibutenetriamine etc., and the molar ratio of the polyamine to the acylated product is 1:2 to 1:8; the catalyst is triethylamine, sodium carbonate or methylpyridine, etc., and the addition amount of the catalyst is 10% of the feeding mass of the polyamine compound; the reacting temperature is 10° C. to 100° C., the reacting time is 2 h to 48 h; and recrystallizing to obtain an intermediate with a dual long-carbon chain: N,N-bis-alkoxyl amide alkylamine, wherein the recrystallizing solvent is ethyl acetate, or anhydrous ethyl alcohol/water mixed solvent (v/v=5:1);

(3) protecting amino of amino acid with a protective reagent, wherein the amino acid is Lys, His, Arg, Asp, Ala, Gly or Orn; the protective reagent is di-tert-butyl dicarbonate ($Boc_2O$), Fmoc N-hydroxysuccinimide ester (Fmoc-OSu) or benzyl chloroformate (CbzCl); the molar ratio of the protective reagent to the amino acid is 1:8 to 8:1; the reaction solvent is water, acetonitrile or acetone, the reaction temperature is 0° C. to 25° C., and the reaction time is 0.5 h to 2 h; and recrystallizing to obtain the peptide head intermediate, wherein the recrystallizing solvent is ethyl acetate/petroleum ether mixed solvent (v/v=3:1);

(4) linking the peptide head intermediate prepared in step (3) with the dual long-carbon chain intermediate prepared in step (2) via amidation: (a) at first, activating the peptide head intermediate to obtain active ester, the activating reagent is 2-(7-azabenzotriazole)-N,N,N',N'-tetramethylureahexafluorophosphate ester (HATU), N,N'-dicyclohexylcarbimide (DCC) or HOBt, the molar ratio of the amino acid to the activating reagent is 1:1 to 1:8, the reaction solvent is dichloromethane, DMF or trichloromethane, the activation time is 0.5 h to 2 h, the activation temperature is 0° C. to 30° C. (b) Adding dichloromethane, DMF or trichloromethane solution of the dual long-carbon chain intermediate into the reactant solution in step a, after ingamidation, the amino of the intermediate and the carboxyl of the peptide head intermediate to generate an amide linkage, the molar ratio thereof is 1:8 to 8:1, the catalyst is 4-dimethylamino pyridine (DMAP) or 1-hydroxybenzotriazole (HOBt), the molar ratio of the addition amount of the catalyst and the dual long-carbon chain intermediate is 1:1 to 1:8, the reaction time is 2 h to 120 h, and the reaction temperature ranges from 20° C. to 60° C.;

(5) removing the amino-protecting reagent, wherein the deprotection reagent is trifluoroacetic acid or 10% $NaHCO_3$, the molar ratio of the deprotection reagent to the lipid compound is 1:1 to 1:2. The deprotection time is 0.5 h to 12 h, and the deprotection temperature ranges from 0° C. to 4° C. Purifying via recrystallizing, wherein the recrystallizing solvent is acetonitrile, anhydrous ethyl alcohol, ultrapure water, ethyl acetate or petroleum ether;

(6) after recrystallization, dissolving the product in chloroform, purifying the crude product with the silica column, and eluting with a methanol/chloroform (volume ratio of 3:1) mixed reagent. Removing the solvent via rotary evaporation at 70° C., and freeze-drying to obtain the bis-alkoxyl amide alkyl cationic peptide lipid compound containing one amino acid head.

(7) synthesizing other bis-alkoxyl amide alkyl cationic peptide lipid using the bis-alkoxyl amide alkyl cationic peptide lipid compound containing one amino acid head as a raw material: after the peptide head intermediate prepared in step (3) and the cationic peptide lipid containing one amino acid head prepared in step (6), are carried out amino acid activation and amidation to obtain the cationic lipid compound with 1 to 4 amino acid heads. Wherein the molar ratio thereof is 1:8 to 8:1, and the specific reactant condition and the purification method are the same as those in steps (4), (5) and (6).

II. A cationic peptide liposome and preparation method thereof

1. A cationic peptide liposome prepared from the bis-alkoxyl amide alkyl cationic peptide lipid, which is uniform and stable liposome formed by dispersing the bis-alkoxyl amide alkyl cationic peptide lipid in a water phase, and has particle sizes of about 100 nm and positive charges on the surface.

2. The preparation method for the bis-alkoxyl amide alkyl cationic peptide liposome comprises the following steps: mixing the bis-alkoxyl amide alkyl peptide lipid compound with an additive in organic solvents, such as chloroform, methylbenzene and methanol, etc. in a molar ratio of 1:1 to 8:1, so that the concentration of the bis-alkoxyl amide alkyl peptide lipid compound is 0.5 mg/ml to 3 mg/ml. Blow-drying the solution under nitrogen to form a uniform film, drying under vacuum for 2 to 24 h (vacuum degree is 0.09 MPa, at normal temperature). And adding ultrapure water, ethanol, phosphate buffer or mixed solution of the three substances, hydrating at temperature of 10° C. to 80° C. for 1 h to 10 h, and ultrasonic vibrating under the ultrasonic frequency of 100 Hz until the solution is clarified and transparent, wherein the concentration of the cationic peptide liposome is 0.5 mg/mL to 3 mg/mL. The additive is dioleoylphosphatidyl ethanolamine (DOPE), dioleoylphosphatidylcholine (DOPC), cholesterol or sucrose ester.

III. A bis-alkoxyl amide alkyl cationic peptide liposome/gene complex and preparation method thereof 1. A bis-alkoxyl amide alkyl cationic peptide liposome/gene complex is uniform and stable nano-particle dispersed in a water phase formed by the bis-alkoxyl amide alkyl cationic peptide liposome and plasmid DNA (pDNA) or small interfering RNA (siRNA), via the electrostatic interaction.

2. The preparation method for the bis-alkoxyl amide alkyl cationic peptide liposome/gene complex comprises the following steps:

(1) dispersing the bis-alkoxyl amide alkyl cationic peptide liposome in the cell culture fluid (DMEM or RPMI1640), and mixing uniformly, so that its concentration ranges from 0.02 μg/μL to 0.16 μg/μL;

(2) diluting 0.5 μg to 1.0 μg of pDNA or siRNA in cell the culture fluid DMEM or RPMI1640, and mixing uniformly, so that the concentration of the plasmid is 0.02 μg/μL;

(3) mixing the two diluted solutions in (1) and (2) uniformly in a mass ratio of the liposome to gene of 1:1 to 8:1, placing it at room temperature for 10 min to 40 min, and obtaining the bis-alkoxyl amide alkyl cationic peptide liposome/gene complex.

IV. Uses of the bis-alkoxyl amide alkyl cationic peptide liposome/gene complex in cell transfection and in-vivo transfection mainly comprise:

1. The peptide liposome genetic vector can enter into cancer cells to complete the transfection of target genes in cells.

2. The cells are human larynx carcinoma epithelial cell (Hep-2) and non-small lung adenocarcinoma cells (A549). The peptide lipid genetic vector system obtained by combining in different nitrogen-phosphorus ratios will be different in transfection efficiency in different cells.

3. The peptide liposome/gene complexes according to the invention are suitable for coding luciferase and green fluorescent protein reporter genes, and are also suitable for siRNA needed by other experiments. The vector can efficiently carry pDNA and siRNA to transfect cells and almost does not have toxicity to the cells.

4. Amino acid or peptide molecules have amino with positive charges and can combine with negatively charged gene substances, and thereby improving the ability of compressing genes by the genetic vector and improving the transfection efficiency of genes.

The effect mechanism of the invention is approximately as below: the bis-alkoxyl amide alkyl cationic peptide liposome/gene complexes provided by the invention, because their cationic peptide lipids have amino acid, or a peptide head, a carbamic acid ester bond and alkyl hydrophobic tail which consists of amino acid, hence they simultaneously have hydrophobic and hydrophilic properties, the hydrophobic part is derived form a dual long-carbon chain, and the hydrophilic part is derived from the lipid head consisting of amino acid or peptide, which has good biocompatibility, since the amino acid or the peptide has a multi-amino structure, it can combine with negatively charged genetic materials (nucleic acid, genes and genetic materials shall be unified) and it has high affinity on cells and nucleic acids, and improve the ability of compressing the genes, thereby it can improve the transfection efficiency of the vector. In addition, the amino acid and the peptide are substances essential to living organisms, which can reduce the toxicity caused by the polar head of the cationic lipid.

Compared with the prior art, the present invention has the following advantages:

1. The synthetic method of the bis-alkoxyl amide alkyl cationic peptide lipid of the present invention is simple, the reaction reagent used in the present invention and the obtained product are non-toxic and pollution-free, and costs of raw materials are low, so it has the nicer popularization; in the reaction process, condition is mild, by-products are few and easy to purify; so it can be widely applied in scientific research and production.

2. The bis-alkoxyl amide alkyl cationic peptide liposomes provided by the invention are rich in positive ions, have the ability of compressing pDNA and siRNA, and can form the nanoscaled cationic liposome/gene complexes. The cationic peptide liposome/gene complexes are acid-sensitive, which are favorable for intracellular release of genes and improving the transfection efficiency. The cationic head of the complexes are peptides, and most of amino acids are essential to human bodies, and the complexes have good biocompatibility and lower toxicity than the traditional quaternary ammonium salt cationic lipids.

3. The bis-alkoxyl amide alkyl cationic peptide liposomes of this invention have good stability, the grain diameter being about 100 nm, Zeta electric potential between 40 mV and 70 mV, they can compress more negatively charged gene substances, improve the in-vitro and in-vivo transfection efficiency, have excellent cytocompatibility and low toxicity, and can be used as a novel efficient low-toxicity non-viral gene vector and a transfection reagent.

4. The bis-alkoxyl amide alkyl cationic peptide liposome/gene complexes of the invention also have good effect on carrying siRNA for gene silencing, with the silencing efficiency being up to 70%.

5. When the peptide liposome/gene complex of the invention is used for in-vivo test, it does not affect the normal growth of mice and does not have toxicity on the livers and kidneys of the mice.

6. Compared with the Germini cationic liposome vector G14 in the Chinese patent application CN103613516A, the bis-alkoxyl amide alkyl cationic peptide liposome of the invention has efficient transfection on tumor cells and lower cytotoxicity.

7. The bis-alkoxyl amide alkyl cationic peptide liposome/gene complex of the invention is convenient to use and is expected to be used as novel gene vectors and transfection reagents for the clinical gene therapy.

DETAILED DESCRIPTION OF THE EMBODIMENTS

Figure 1:
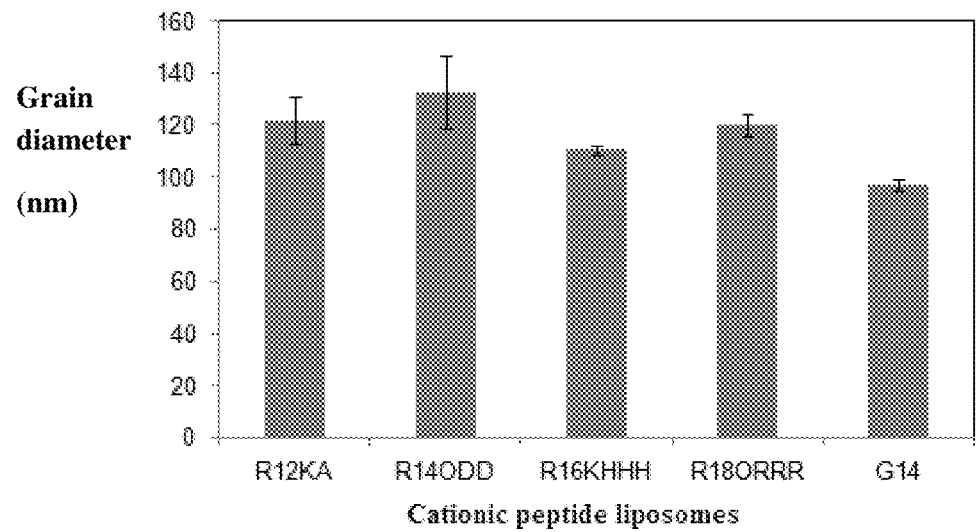
FIG. 1 is a grain diameter detection diagram of cationic peptide liposomes $R_{12}KA$, $R_{14}ODD$, $R_{16}KHHH$ and $R_{18}ORRR$.

In order to further understand the invention, the implementation plan of the invention is set out in combination with the embodiment, however, these statements are only used for further stating the characteristics and advantages of the invention, instead of limiting the claim of the invention.

In the Description, the lipid compound N,N-didodecylalcoxyl amide ethyl lysine alanine amide is expressed as $R_{12}KA$, the lipid compound N,N-ditetradecylalcoxyl amide ethyl ornithine dipolyaspartic acid amide is expressed as $R_{14}ODD$, the peptide lipid compound N,N-dihexadecylalcoxyl amide ethyl lysine tri-poly-histidine amide is expressed as $R_{16}KHHH$, and the lipid compound N,N- dioctadecylalcoxyl amide ethyl ornithine tri-poly-arginine amide is expressed as $R_{18}ORRR$.

Embodiment 1

The synthetic method for the cationic peptide lipid compound $R_{12}KA$ comprises the following steps:

(1) 20 mmoL of carbonyl diimidazole and 200 mmoL of dodecanol (the molar ratio of 1:10) by using 200 mL of dichloromethane solution are dissolved, reacting at temperature of 60° C. for 2 h, and generating a monosubstituted intermediate. The dichloromethane solution of diethylenetriamine is dripped into the above reactant solution (a molar ratio of diethylenetriamine to acylation product is 1:2), the equimolar amount of triethylamine as the catalyst is added, reacting at temperature of 100° C. for 2 h, and generating a disubstituted intermediate. After the reaction being completed, filter, and carry out rotary evaporation to obtain white transparent viscous liquid. And recrystallize by using ethyl acetate to purify for 3 times, and obtain a white powder disubstituted long-carbon chain intermediate $R_{12}$.

(2) Weigh 2 mmol of L-Lys and dissolve it in 15 mL of acetonitrile, 6 mmol of $Boc_2O$ is dissolved in acetonitrile and dripped into lysine acetonitrile solution, stirring at 25° C. and reacting for 2 h, then add 6 mmol of Fmoc-Osu acetonitrile solution, continuing to react for 6 h, after the reaction being completed, carry out rotary evaporation to remove solvent, recrystallizing by using ethyl acetate/petroleum ether mixed solvent (v/v=3:1) to obtain a peptide head intermediate Fmoc-L-Lys(Boc)-OH.

(3) 1 mmol of the peptide head intermediate Fmoc-L-Lys(Boc)-OH and an activating reagent HATU are dissolved in dichloromethane solution in a molar ratio of 1:2, activating at 0° C. for 2 h, then add the dichloromethane solution of the long-carbon chain intermediate $R_{12}$ (a molar ratio of lysine to the long-carbon chain intermediate is 1:8), add 1 mmol of catalyst DMAP, carry out amidation reaction at temperature of 20° C. for 120 h, after the reaction being completed, carry out rotary evaporation at temperature of 70° C. to dry the solvent, dissolve in the dichloromethane/trifluoroacetic acid (=2/1) solvent, place at temperature of 4° C. for 8 h, removing the protecting group Boc, dissolve in 10% $NaHCO_3$ solvent, react for 1 h, and remove the Fmoc group.

(4) The product is recrystallized by using ethyl acetate for 2 times and is recrystallized by using acetonitrile for 2 times. The product is dissolved in chloroform, the crude product is purified by using the silica column, and eluted by using the methanol/chloroform (the volume ratio of 3:1) mixed reagent. And removed the solvent via rotary evaporation at temperature of 70° C., and freeze-dried to obtain the bis-alkoxyl amide alkyl cationic peptide lipid containing a lysine head.

(5) 5 mmol of alanine is dissolved in tetrahydrofuran, 10 mmol of $Boc_2O$ is dissolved in tetrahydrofuran, dripped into alanine, adding 5 mmol of DMAP, and reacting at temperature of 0° C. for 2 h. And after the reaction being completed, remove the solvent via rotary evaporation at temperature of 70° C., and recrystallize by using acetonitrile for 2 times to obtain a peptide head intermediate L-Ala(Boc)-OH.

(6) The bis-alkoxyl amide alkyl cationic peptide lipid compound containing a lysine head, which is prepared in step (4), with the amino-protected peptide head intermediate L-Ala(Boc)-OH, prepared in step (5), in a molar ratio of 8:1, are reacted as the raw materials, and carried out amino acid activation and amidation to obtain dipeptide head cationic peptide lipid $R_{12}KA$ containing one Lys and one Ala, wherein the specific reaction condition and the purification method are the same as those in steps (3) and (4).

The structural characterization is as below: $^1H$ NMR (400 MHz, $CD_3OD$) δ: 0.95 (6H, $CH_3$), 1.32 (28H, (($CH_2)_7$)), 1.49 (4H, $CH_2CH_2O$), 3.32 (6H, $CONHCH_2$, $CH_2NH$), 3.89 (4H, NH), 4.08 (4H, $CH_2CH_2O$), 4.95 (6H, $NH_2$). $^{13}C$ NMR (400 MHz, $CD_3OD$) δ 17.25 ($CH_3$), 25.44 ($CH_3CH_2$), 33.01 (($CH_2)_8$), 35.12 ($CHCH_2$), 35.92 ($CH_3CH_2CH_2$), 42.10 ($NHCH_2$), 57.03 (NHCH, $NH_2CH$), 68.92 ($CH_2NH_2$), 162.13 (COONH), 172.78 (NCOCH), 177.35 (NHCOCH). IR v/cm$^{-1}$: 3323.29 ($v_{NH}$), 2924.56 ($v_{CH}$), 1691.23 ($v_{C=O}$), 1545.37 ($δ_{NH}$), 1270.30-1195.36 ($v_{COC}$, $v_{CN}$).

Embodiment 2

The synthetic method for the cationic peptide lipid compound $R_{14}ODD$ comprises the following steps:

(1) 40 mmoL of carbonyl diimidazole and 240 mmoL of tetradecanol (the molar ratio of 1:6) are dissolved by using 200 mL of dichloromethane solution, reacting at temperature of 60° C. for 2 h, and generating a monosubstituted intermediate. The dichloromethane solution of diethylenetriamine was dripped into the above reactant solution (a molar ratio of diethylenetriamine to acylation product is 1:1), add the equimolar amount of triethylamine as the catalyst, react at temperature of 40° C. for 10 h, and generate a disubstituted intermediate. After reaction being completed, filter, and carry out rotary evaporation to obtain white transparent viscous liquid. And recrystallize by using the mixed solvent of ethyl acetate and ethanol (the volume ratio of 5:1) to purify for 3 times, and obtain a white powder disubstituted long-carbon chain intermediate $R_{14}$.

(2) Weigh 50 mmol of L-Orn and dissolve in 150 mL of water, 100 mmol of $Boc_2O$ is dissolved in water and dripping into ornithine aqueous solution, stirring at temperature of 30° C. for reacting for 2 h, add 100 mmol of Fmoc-Osu acetonitrile solution, continue to react for 10 h, after reaction being completed, carry out rotary evaporation to remove solvent, recrystallize by using an ethyl acetate/petroleum ether (2:1) system to obtain a peptide head intermediate L-Fmoc-Orn(Boc)-OH.

(3) 20 mmol of protected ornithine peptide head intermediate L-Fmoc-Orn(Boc)-OH and an activating reagent HATU are dissolved in dichloromethane solution in a molar ratio of 1:4, activating at temperature of 0° C. for 2 h, then add the dichloromethane solution of the long-carbon chain intermediate $R_{14}$ (a molar ratio of ornithine to long-carbon chain intermediate is 1:7), add 1.5 mmol of catalyst DMAP, carry out amidation reaction at temperature of 40° C. for 2 h, after reaction being completed, carry out rotary evaporation to dry the solvent, the product is dissolved by using the dichloromethane/trifluoroacetic acid (volume ratio=3/1) solvent, placing at temperature of 4° C. for 8 h, and removing the protecting group Boc. And dissolve by using dioxane/$NaHCO_3$ solvent, react for 12 h, and remove the Fmoc group.

(4) Using petroleum ether recrystallize for 2 times, using the mixed solvent of ethanol and water (5:1) recrystallize for 2 times, the product is dissolved in chloroform, purifying the crude product by using the silica column, and eluting by using the methanol/chloroform (the volume ratio of 3:1) mixed reagent. And remove the solvent via rotary evaporation at temperature of 70° C., and freeze-dry to obtain the cationic peptide lipid compound containing an ornithine head.

(5) 20 mmol of aspartic acid and the protective reagent $Boc_2O$ are dissolved in water in a molar ratio of 8:1, add 20 mmol of HOBt, and react at temperature of 60° C. for 1 h. And after reaction being completed, remove the solvent via rotary evaporation at temperature of 70° C., and recrystallize by using petroleum ether for 3 times to prepare a peptide head intermediate L-Asp(Boc)-OH.

(6) The bis-alkoxyl amide alkyl cationic peptide lipid compound containing a lysine head, prepared in step (4), with the amino-protected peptide head intermediate L-Asp(Boc)-OH, prepared in step (5), in a molar ratio of 1:4, are reacted as the raw materials, and carried out amino acid activation and amidation to obtain tripeptide head cationic peptide lipid $R_{12}ODD$ containing one Orn and two Asp, wherein the specific reaction condition and the purification method are the same as those in steps (3) and (4).

The structural characterization is as below: $^1H$ NMR (400 MHz, $CD_3OD$) δ: 0.902 (s, 6H, $CH_3$); 1.293 (t, 36H, J=6.8, $CH_3CH_2$); 1.612 (s, 4H, $CH_2CH_2O$); 4.013 (s, 4H, $CH_2CH_2O$); 3.256 (s, 6H, $NHCH_2$); 2.980 (s, 8H, $CH_2N$); 3.544 (t, 3H, J=6.0, COCH); 1.893-1.911 (s, 6H, $CHCH_2CH2$); 1.536 (s, 6H, $CHCH_2CH_2CH_2$); 1.724 (s, 4H, $CH_2CH_2NH$). $^{13}C$ NMR (400 MHz, $CD_3OD$) δ 161.662 (C=O), 173.20 (COCH), 64.999 (CHNH), 26.658 (NHCH $CH_2CH_2$), 30.69 ($CH_2CH_2NH$), 48.243 ($NHCH_2$), 31.879 ($CH_2CH_2CH_3$), 30.063-28.785 (($CH_2)_{10}$), 26.872-25.843 ($CH_2CH_3$), 13.253 ($CH_3$). IR $v/cm^{-1}$: 3322.78 ($v_{NH}$), 2921.78 ($v_{CH}$), 1690.90 ($v_{C=O}$), 1542.37 ($δ_{NH}$), 1269.35-1195.36 ($v_{COC}$, $v_{CN}$).

Embodiment 3

The synthetic method for the cationic peptide lipid compound $R_{16}KHHH$ comprises the following steps:

(1) 5 mmol of carbonyl diimidazole is dissolved in chloroform, add 0.5 mmol of hexadecanol, add 40 mmol of chloroform solution of dipropylenetriamine, add 2 mmol of methylpyridine as the catalyst, and react at temperature of 10° C. for 48 h to obtain a disubstituted long-carbon chain intermediate compound. After reaction being completed, filter, and carry out rotary evaporation to obtain white transparent viscous liquid. And recrystallize by using the mixed solvent of ethyl acetate and ethanol (volume ratio of 5:1) to purify for 3 times, and obtain a white powder disubstituted long-carbon chain intermediate $R_{16}$.

(2) Weigh 2 mmol of L-Lys and dissolve it in 15 mL of acetonitrile, 6 mmol of $Boc_2O$ is dissolved in acetonitrile and dripped into lysine acetonitrile solution, stirring and reacting at temperature of 60° C. for 3 h, then add 12 mmol of Fmoc-Osu acetonitrile solution, continue to react for 8 h, after reaction being completed, carry out rotary evaporation to remove solvent, recrystallize by using ethyl acetate to obtain L-Fmoc-Lys(Boc)-OH.

(3) The protected lysine and the activating reagent in a molar ratio of 1:1 are dissolved in acetone, react at temperature of 40° C. for 0.5 h, adding the long-carbon chain intermediate $R_{16}$ with the molar ratio 8 times that of the lysine, adding 2 mmol of pyridine, and reacting at temperature of 40° C. for 48 h. After reaction being completed, carry out rotary evaporation to remove the solvent. Dissolve the product by using the dichloromethane/trifluoroacetic acid (=3/1) solvent, place at temperature of 4° C. for 8 h, and remove the protecting group Boc. And dissolve by using dioxane/$NaHCO_3$ solvent, reacting for 12 h, and remove the Fmoc group.

(4) Using petroleum ether recrystallize for 3 times, the product is dissolved in chloroform, purify the crude product by using the silica column, and elute by using the methanol/chloroform (3:1) mixed reagent. And remove the solvent via rotary evaporation at temperature of 70° C., and freeze-dry to obtain the cationic peptide lipid compound containing an lysine head.

(5) 5 mmol of His is dissolved in 25 mL of distilled water, the protective reagent CbzCl is dissolved in 50 ml of tetrahydrofuran in a molar ratio of 1:5, dripping both slowly, mixing uniformly, adding 2 mmol of DMAP, and reacting at temperature of 20° C. for 4 h. And after reaction being completed, remove the solvent via rotary evaporation at temperature of 70° C., and recrystallize by using acetonitrile for 3 times to prepare a peptide head intermediate L-His(CbzCl)—OH.

(6) The bis-alkoxyl amide alkyl cationic peptide lipid compound containing a lysine head, prepared in step (4), with the amino-protected peptide head intermediate L-His(CbzCl)—OH, prepared in step (5), in a molar ratio of 1:6, are reacted as raw materials, and carried out amino acid activation and amidation, wherein the specific reaction condition is the same as that in step (3). The product is added into 20 mL of 10% $NaHCO_3$ aqueous solution, and reacted for 4 h to remove the CbzCl protecting group. And obtain a tetrapeptide head cationic peptide lipid $R_{16}KHHH$ containing one Lys and three His, wherein the purification condition is the same as that in step (4).

The structural characterization is as below: $^1H$ NMR (400 MHz, $CD_3OD$) δ: 0.877 (s, 6H, $CH_3$); 1.286 (t, 44H, J=6.8, $CH_3CH_2$); 1.486 (s, 4H, $CH_2CH_2NH$); 1.731 (s, 6H, $CH_2CH_2NH_2$); 1.881-1.912 (s, 6H, $CHCH_2CH_2$); 2.966-2.993 (s, 4H, $CH_2NH_2$); 3.091 (t, 6H, J=6.0, $CH_2NH$); 3.304 (s, 2H, $CHCH_2NH$); 3.963 (s, 2H, $NH_2CH$); 4.045 (s, 2H, $OCH_2CH_2$); 4.35 (s, 1H, CHNH); 4.953 (s, 1H, $OCHCH_2$). $^{13}C$ NMR (400 MHz, $CD_3OD$) δ 172.34 (CONH), 157.5 ($COOCH_2$), 168.0 (NHCOCH), 156.2 (COOCH), 53.29 ($CHNH_2$), 30.15-31.06 ($CHCH_2CH_2$), 22.37 ($CHCH_2CH_2$), 27.82 ($CHCH_2CH_2$), 39.99 ($CH_2NH_2$), 54.9 (CHNH), 38.82 (NH $CH_2CH$), 72.07 (CH2CHO), 62.9 ($CH2CH_2O$), 38.35 ($CH_2NH$), 29.92-28.45 (($CH_2)_{12}$, $NHCHCH_2$), 32.094 ($CH_2CH_2CH_3$), 22.37 ($CH_2CH_3$), 12.402 ($CH_3$). IR $v/cm^{-1}$: 3365 ($v_{NH}$), 2929-2848 ($v_{CH}$, $v_{CH2}$), 1654 ($v_{C=O}$), 1247 ($v_{CN}$).

Embodiment 4

The synthetic method for the cationic peptide lipid $R_{18}ORRR$ compound comprises the following steps:

(1) 10 mmol of carbonyl diimidazole is dissolved in chloroform, 0.5 mmol of octadecanol is added, 40 mmol of chloroform solution of dipropylenetriamine is added, 2 mmol of methylpyridine as the catalyst is added, and reacted at temperature of 10° C. for 48 h to obtain a disubstituted long-carbon chain intermediate compound. After reaction being completed, filter, and carry out rotary evaporation to obtain white transparent viscous liquid. And using the mixed solvent of ethyl acetate and ethanol recrystallize to purify for 3 times, and obtain a white powder disubstituted long-carbon chain intermediate $R_{18}$.

(2) Weigh 50 mmol of L-Orn and dissolve it in 150 mL of water, 100 mmol of $Boc_2O$ is dissolved in water and dripped into ornithine aqueous solution, stirring and reacting at temperature of 30° C. for 2 h, adding 100 mmol of Fmoc-Osu acetonitrile solution, continuing to react for 10 h, after reaction being completed, carry out rotary evaporation to remove solvent, using an ethyl acetate/petroleum ether (volume ratio of 2:1) system recrystallize to obtain a peptide head intermediate L-Fmoc-Orn(Boc)-OH.

(3) 10 mmol of protected ornithine peptide head intermediate L-Fmoc-Orn(Boc)-OH and an activating reagent HATU are dissolved in dichloromethane solution in a molar ratio of 1:4, activating at temperature of 0° C. for 2 h, then he dichloromethane solution of the long-carbon chain intermediate $R_{18}$ (a molar ratio of the ornithine to the long-carbon chain intermediate is 4:1) is added, 0.5 mmol of catalyst DMAP is added, carrying out amidation reaction at temperature of 40° C. for 2 h, after reaction being completed, carry out rotary evaporation to dry the solvent, the product is dissolved by using the dichloromethane/trifluoroacetic acid (volume ratio=3/1) solvent, placing at temperature of 4° C. for 8 h, and removing the protecting group Boc. And dissolve in dioxane/$NaHCO_3$ solvent, reacting for 12 h, and remove the Fmoc group.

(4) Using petroleum ether recrystallize for 2 times, using the mixed solvent of ethanol and water (the volume ratio of 5:1) recrystallize for 2 times, the product is dissolved in chloroform, purify the crude product by using the silica column, and elute by using the methanol/chloroform (the volume ratio of 3:1) mixed reagent. And remove the solvent via rotary evaporation at temperature of 70° C., and freeze-dry to obtain the cationic peptide lipid compound containing an ornithine head.

(5) Weigh 10 mol of Arg and it is dissolved in 60 mL of mixed solvent of acetonitrile and water (acetonitrile:water=3:1), 30 mmol of $Boc_2O$ is dissolved in acetonitrile and dripped into aspartic acid acetonitrile solution, stirring and reacting at temperature of 20° C. for 4 h, add 30 mmol of Fmoc-Osu into the above solution, continue to react at temperature of 20° C. for 3 h, after reaction being completed, carry out rotary evaporation to remove solvent, recrystallize by using an ethyl acetate/petroleum ether (volume ratio of 2:1) system to obtain a peptide head intermediate L-Fmoc-Arg(Boc)-OH.

(6) The bis-alkoxyl amide alkyl cationic peptide lipid compound containing a ornithine head, prepared in step (4), with the amino-protected peptide head intermediate L-Fmoc-Arg(Boc)-OH, prepared in step (5), in a molar ratio of 2:1, are reacted as the raw materials, and carried out amino acid activation and amidation to obtain dipeptide head cationic peptide lipid $R_{18}OR$ containing one Orn and one Arg, wherein the specific reaction condition and the purification method are the same as those in steps (3) and (4).

(7) The bis-alkoxyl amide alkyl cationic peptide lipid $R_{18}OR$ compound containing a dipeptide head, prepared in step (6), with the amino-protected peptide head intermediate L-Fmoc-Arg(Boc)-OH, prepared in step (5), in a molar ratio of 1:4, are reacted as the raw materials, and carried out amino acid activation and amidation to obtain tetrapeptide head cationic peptide lipid $R_{18}ORRR$ containing one Orn and three Arg, wherein the specific reaction condition and the purification method are the same as those in steps (3) and (4).

The structural characterization is as below: $^1H$ NMR (400 MHz, $CDCl_3$) δ: 0.866 (s, 6H, $CH_3$); 1.244 (t, 52H, J=6.8, $CH_3CH_2$); 1.564 (s, 4H, $CH_2CH_2O$); 3.969 (s, 4H, $CH_2CH_2O$); 2.945 (s, 8H, $CH_2N$); 2.871 (t, 3H, J=6.0, COCH); 1.906-1.998 (s, 6H, $CHCH_2CH2$); 1.564 (s, 6H, $CHCH_2CH_2CH_2$); 1.660 (s, 4H, $CH_2CH_2NH$). $^{13}C$ NMR (400 MHz, $CD_3OD$) δ 46.011 (CHNH), 22.888 (NHCH $CH_2CH_2$), 14.285 ($CH_2CH_2NH$), 32.146 ($CH_2CH_2CH_3$), 29.594-29.971 (($CH_2)_{14}$), 25.146-26.038 ($CH_2CH_3$), 8.898 ($CH_3$). IR v/$cm^{-1}$: 3420.78 ($v_{NH}$), 2925.20 ($v_{CH}$), 1679.13 ($v_{C=O}$), 1261.32 ($v_{CN}$).

Embodiment 5 Preparation of Cationic Peptide Liposome by $R_{12}KA$

Weighed 1 mg of cationic peptide lipid $R_{12}KA$, with cholesterol as an additive in the same molar ratio, are dissolved in 1 mL of mixed solvent of methanol and trichloromethane (a mixed ratio is 2:1 (volume ratio)), after fully dissolving, blow to form a uniform film under nitrogen, dry under vacuum for 5 h to volatilize solvent completely (vacuum degree is −0.09 MPa, normal temperature), after dissolving by using 100 μL of anhydrous ethyl alcohol, add 900 μL of ultrapure water, so that the concentration of liposomes is 1 mg/mL, hydrating at temperature of about 80° C. for 1 h, and carry out ultrasonic vibrate at ultrasonic frequency of 100 Hz until the solution is clarified and transparent to obtain the cationic peptide liposome.

Embodiment 6 Preparation of Cationic Peptide Liposome by $R_{14}ODD$ 0.5 mg of cationic peptide lipid $R_{14}ODD$ is weighed and dissolved in 1 mL of trichloromethane, add lecithin as an additive (a molar ratio of $R_{14}ODD$ to lecithin is 1:2), after fully dissolving, blow to form a uniform film under nitrogen, dry under vacuum for 12 h to volatilize solvent completely (vacuum degree is −0.09 MPa, normal temperature), immerse by using 1 mL of ultrapure water for 2 h to drop a film off, and carry out ultrasonic vibrate repeatedly at temperature of about 55° C. (vibrate frequency is 100 Hz) until the solution is clarified and transparent to obtain the cationic peptide liposome with the concentration of 0.5 mg/mL.

Embodiment 7 Preparation of Cationic Peptide Liposome by $R_{16}KHHH$

Weighed 5 mg of cationic peptide lipid $R_{16}KHHH$, with DOPE as an additive (a molar ratio of $R_{16}KHHH$ to DOPE is 8:1) are dissolved in 5 mL of trichloromethane, after fully dissolving, blow to form a uniform film under nitrogen, dry under vacuum for 8 h to volatilize solvent completely (vacuum degree is −0.09 MPa, normal temperature), add 5 mL of phosphate buffer, hydrating at temperature of 30° C. for 8 h, and carry out ultrasonic vibrate at ultrasonic frequency of 100 Hz until the solution is clarified and transparent to obtain the cationic peptide liposomes with the concentration of 5 mg/mL.

Embodiment 8 Preparation of Cationic Peptide Liposome by $R_{18}ORRR$

Cationic peptide lipid $R_{18}ORRR$ and sucrose ester S070 as an additive (cationic peptide liposome is 2 mg) in a molar ratio of 3:1 are accurately weighed, dissolved in 1 mL of mixed solvent of methanol and trichloromethane (methanol:trichloromethane=1:2 (volume ratio)), after fully dissolving, blowing to form a uniform film under nitrogen, drying under vacuum for 4 h to volatilize solvent completely (vacuum degree is −0.09 MPa, normal temperature), adding 200 μL of anhydrous ethyl alcohol at temperature of about 55° C. to drop the film off, adding 800 μL of buffer solution, and carrying out ultrasonic vibrate repeatedly at temperature of about 40° C. (ultrasonic frequency is 100 Hz) until the solution is clarified and transparent to obtain the cationic peptide liposome with the concentration of 2 mg/mL.

Figure 2:
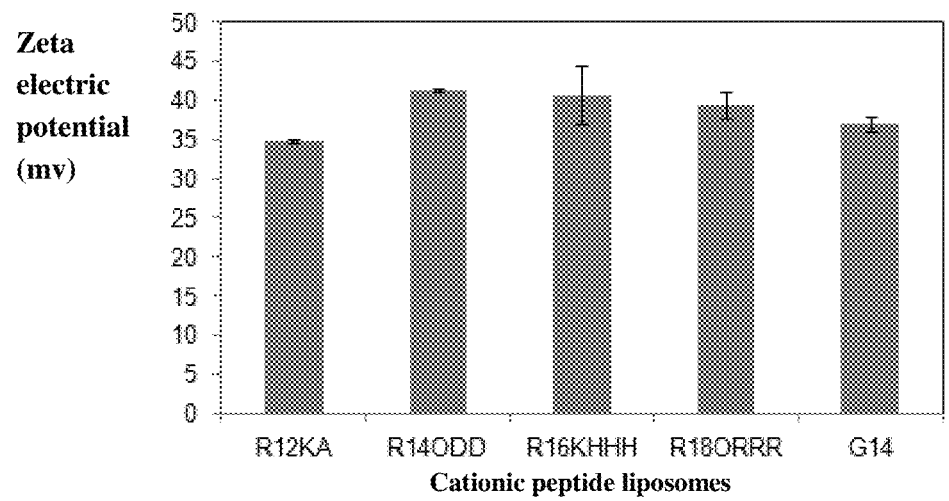
FIG. 2 is a Zeta electric potential detection diagram of cationic peptide liposomes $R_{12}KA$, $R_{14}ODD$, $R_{16}KHHH$ and $R_{18}ORRR$.

Embodiment 9 Detection of Grain Diameters and Zeta Electric Potentials of Liposomes The grain diameters and Zeta electric potentials of the prepared cationic peptide liposomes are measured by using the laser scattering particle size analyzer (HORIBA nano-particle size analyzer SZ-100) at the light scattering angle of 90° at temperature of 25° C., take 20 μL of cationic peptide liposomes prepared in embodiments 1 to 8 by using the pipette, and dilute in 1 mL of ultrapure water to detect grain diameters and Zeta electric potentials, and the results are shown in FIG. 1 and FIG. 2. FIG. 1 is the average grain diameter of 4 cationic peptide liposomes, and FIG. 2 is the Zeta electric potentials of 4 cationic peptide liposomes.

The result shows that the grain diameters of the liposomes formed by 4 cationic peptide lipids are about 100 nm, which are within the range of the effective grain diameter (<1 μm) of transfection. The absolute values of Zeta electric potentials are more than 30 mV, and the static stability is high.

Embodiment 10 Preparation of $R_{12}KA$ liposome/DNA Complex

The cationic peptide liposome is prepared via the method described in the embodiment 5. 0.5 μg of 1 mg/mL of liposome $R_{12}KA$ is weighed, diluted to 25 μL by using the serum-free DMEM culture medium; 0.5 μg of 0.5 mg/mL of plasmid DNA is weighed, and diluted to 25 μL by using the serum-free DMEM culture medium; mix the two diluents (a mass ratio of liposome to DNA is 1:1), carry out vortex oscillation, and incubate at room temperature for 10 min to obtain the $R_{12}KA$ liposome/DNA complex.

Embodiment 11 Preparation of $R_{14}ODD$ Liposome/DNA Complex

The cationic peptide liposome is prepared via the method described in the embodiment 6. 1 μg of 0.5 mg/mL of liposome $R_{14}ODD$ is weighed, diluted to 25 μL by using the serum-free DMEM culture medium; taking 0.5 μg of 0.5 mg/ml of plasmid DNA, and diluted to 25 μL by using the serum-free DMEM culture medium; mix the two diluents (a mass ratio of liposome to DNA is 2:1), carry out vortex oscillation, and incubate at room temperature for 20 min to obtain the $R_{14}ODD$ liposome/DNA complex.

Embodiment 12 Preparation of $R_{16}KHHH$ Liposome/DNA Complex

The cationic peptide liposome is prepared via the method described in the embodiment 7. 3.0 μg of 1.5 mg/mL of liposome $R_{16}KHHH$ is weighed, diluted to 25 μL by using the serum-free DMEM culture medium; 0.5 g of 0.5 mg/ml of plasmid DNA is weighed, and diluted to 25 μL by using the serum-free DMEM culture medium; mix the two diluents (a mass ratio of liposome to DNA is 6:1), carry out vortex oscillation, and incubate at room temperature for 30 min to obtain the $R_{16}KHHH$ liposome/DNA complex.

Embodiment 13 Preparation of $R_{18}ORRR$ Liposome/DNA Complex

The cationic peptide liposome is prepared via the method described in the embodiment 8. 4.0 g of 3.0 mg/mL of liposome $R_{18}ORRR$ is weighed, diluted to 25 μL by using the serum-free DMEM culture medium; 0.5 μg of 0.5 μg/L of plasmid DNA is weighed, and diluted to 25 μL by using the serum-free DMEM culture medium; mix the two diluents (a mass ratio of liposome to DNA is 8:1), carry out vortex oscillation, and incubate at room temperature for 40 min to obtain the $R_{18}ORRR$ liposome/DNA complex.

Embodiment 14 Preparation of Cationic Peptide Liposome/siRNA Complex

The cationic peptide liposome is prepared via the methods described in embodiments 5 to 8. 0.9 μg of 1 mg/mL of liposome $R_{14}ODD$ is weighed, diluted to 25 μL by using the serum-free DMEM culture medium; 0.3 μg of 0.3 μg/L of siRNA is weighed, and diluted to 25 μL by using the serum-free DMEM culture medium; mixing the two diluents (a mass ratio of liposome to siRNA is 3:1), carry out vortex oscillation, and incubate at room temperature for 20 min to obtain the $R_{14}ODD$ liposome/DNA complex.

Embodiment 15 Electrophoresis Delay Experiment of Combining Liposome with Plasmid DNA The charge ratio of the cationic peptide liposome and the plasmid DNA in different mass ratios is detected via agarose gel electrophoresis delay experiment, to further arrive at the effective ratio of compression. The cationic peptide liposome and the plasmid DNA sequentially are diluted in mass ratios of 0:1, 0.5:1, 1:1, 2:1, 3:1, 4:1, 6:1 and 8:1 in 15 μL of RMPI 1640 culture solution, slightly carrying out vortex oscillation for uniform mixing, incubating at room temperature for 20 min, adding 15 μL of the complex of the cationic peptide liposome and plasmid DNA into 2 μL of 6×DNA Loading buffer and mixing uniformly, loading samples on the sample loading well of 1.2% agarose gel in order, and carrying out electrophoresis at voltage of 90V for 40 min. Nucleic acid dye liquor NA-Red is added during gel making, and directly observe the DNA delay condition in the gel imaging system Gene Genius Bio-imaging System (SYN-GENE Company) after electrophoresis is finished. The electrophoresis result is shown in the FIG. 3, wherein the channels 1 to 8 are liposome/DNA complex in a mass ratio of cationic peptide liposome to DNA of 0:1, 0.5:1, 1:1, 2:1, 3:1, 4:1, 6:1 and 8:1 respectively. A is an electrophoretogram of combining the cationic peptide liposome $R_{12}KA$ and DNA, B is an electrophoretogram of cationic peptide liposome $R_{14}KDD$ and DNA, C is an electrophoretogram of cationic peptide liposome $R_{16}KHHH$ and DNA, and D is an electrophoretogram of cationic peptide liposome $R_{18}ORRR$ and DNA.

Figure 3:
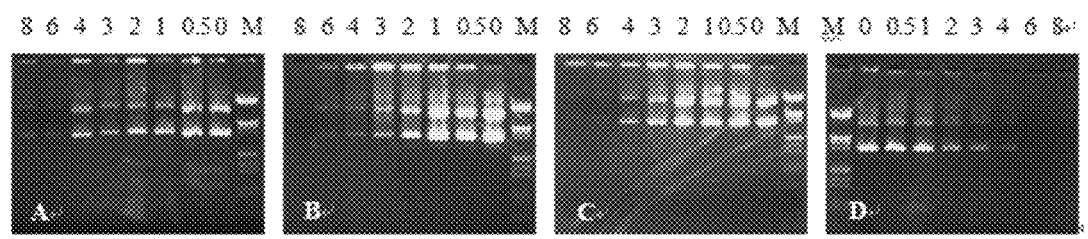
FIG. 3 is an electrophoresis delay experiment result diagram of cationic peptide liposomes $R_{12}KA$, $R_{14}ODD$, R16KHHH and $R_{18}ORRR$ and plasmid DNA.

The result of the FIG. 3A shows that with the increase of mass of liposomes, the delay effect of DNA is increasingly obvious, and DNA has delayed completely in a mass ratio of 6:1. The result of the FIG. 3B shows that with the increase of mass of liposomes, the delay effect of DNA is increasingly obvious, and DNA has delayed completely in a mass ratio of 8:1. The result of the FIG. 3 C shows that with the increase of mass of liposomes, the delay effect of DNA is increasingly obvious, and DNA has delayed completely in a mass ratio of 6:1. The result of the FIG. 3 D shows that with the increase of mass of liposomes, the delay effect of DNA is increasingly obvious, and DNA has delayed completely in a mass ratio of 6:1.

Embodiment 16 In-Vitro Biological Assessment Experiment (1) Experiment of Carrying pGFP-N2 Plasmid to Transfect Cells Hep-2 and NCI-H460 cells are planted in a 24-well cell culture plate in the cell concentration of about of $1.0 \times 10^5$/well, incubated for 24 h, so that the cell density is up to 80 to 90% on the transfection date. The liposome and the plasmid pGFP-N2 were complexed in ratios of 1:1, 2:1, 3:1, 4:1, 6:1 and 8:1 to reach the total volume of 100 μL. The complex is added into the cell culture plate, culturing for 4 h to 5 h, replaced with the culture medium containing 10% serum and antibiotics, and cultured for 48 h. The product GFP expressed by green fluorescent protein can emit green fluorescence with the peak of 508 nm, and using the inverted fluorescence microscope can carry out analysis of gene expression. Positive cells emit bright green fluorescence, negative cells will not, the more GFP positive cells indicate stronger signals and higher transfection rate. The observation multiples are 20×10.

Figure 4:
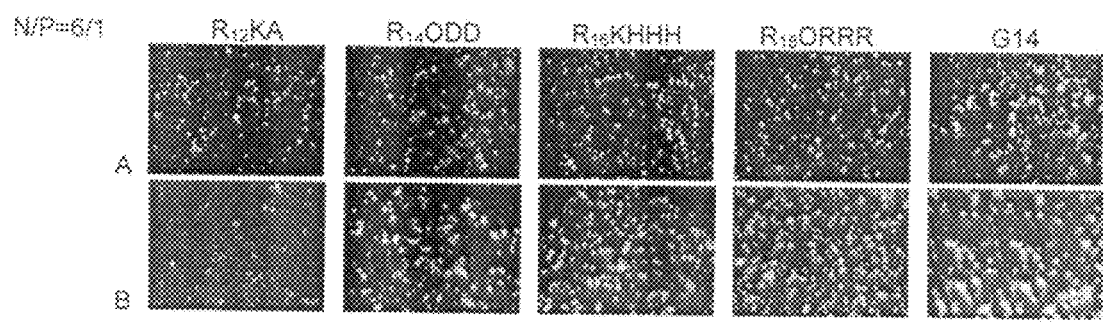
FIG. 4 is a green fluorescent protein expression diagram of carrying pGFP-N2 plasmid to transfect NCI-H460 cells (human giant cell lung cancer cell, FIG. 4A) and Hep-2 cells (human larynx carcinoma cells, FIG. 4B) by using the cationic peptide liposomes detected by the inverted fluorescence microscope.
Figure 5:
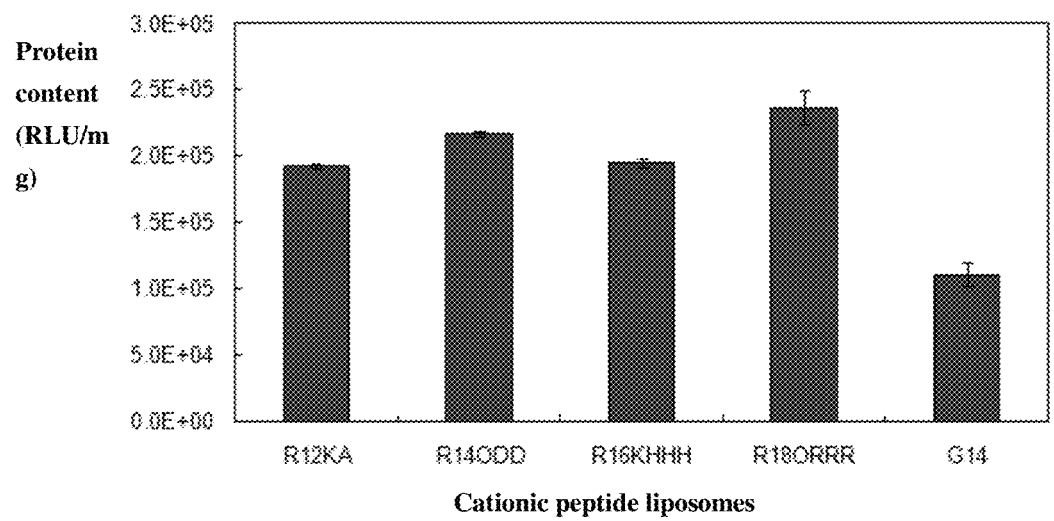
FIG. 5 is a luciferase expression diagram of carrying pGL-3 plasmid to transfect NCI-H460 cells by using the cationic peptide liposomes detected by the microplate reader.

The result is shown in FIGS. 4 and 5, a mass ratio of the liposome and DNA is 6:1, FIG. 4 is the transfection result of the cationic peptide liposome transfected NCI-H460 cells; and FIG. 5 is the transfection effect of cationic peptide liposome transfected Hep-2 cells. The results indicate that the liposome can efficiently transfect NCI-H460 and Hep-2 cells, and compared with the Gemini liposome genetic vector G14, the transfection efficiency is improved by 50%.

(2) Experiment of Carrying pGL-3 Plasmid to Transfect Cells

The cell culture method is the same as the above step (1). The liposome and the plasmid pGL3 are complexed in ratios of 1/1, 2/1, 3/1, 4/1, 6/1 and 8/1 to reach the total volume of 100 μL. The complex is added into the cell culture plate, shaking the culture plate, and mixing gently and uniformly. It is cultured in 5% $CO_2$ (incubator) at temperature of 37° C. for 4 to 5 h, replaced with the culture medium containing 10% serum and antibiotics, and cultured for 48 h. The cells was washed after being transferred with DPBS once, 600 μL of lysate is added into each well, transferring to the 96-well white board after 20 min, adding 80 μL of Promega E151A detection solution in each well. The relative enzyme activity is detected by utilizing the Synergy 2 multifunctional microplate reader (BioTek). Total protein content via control is measured based on the Pierce BCA Protein Assay kit of the Thermoelectricity Corporation. After measuring protein, the transfection efficiency can be expressed as RLU/mg protein. The commercial gene transfection reagents Lipofectamine 2000 and DOTAP are used as control.

Figure 6:
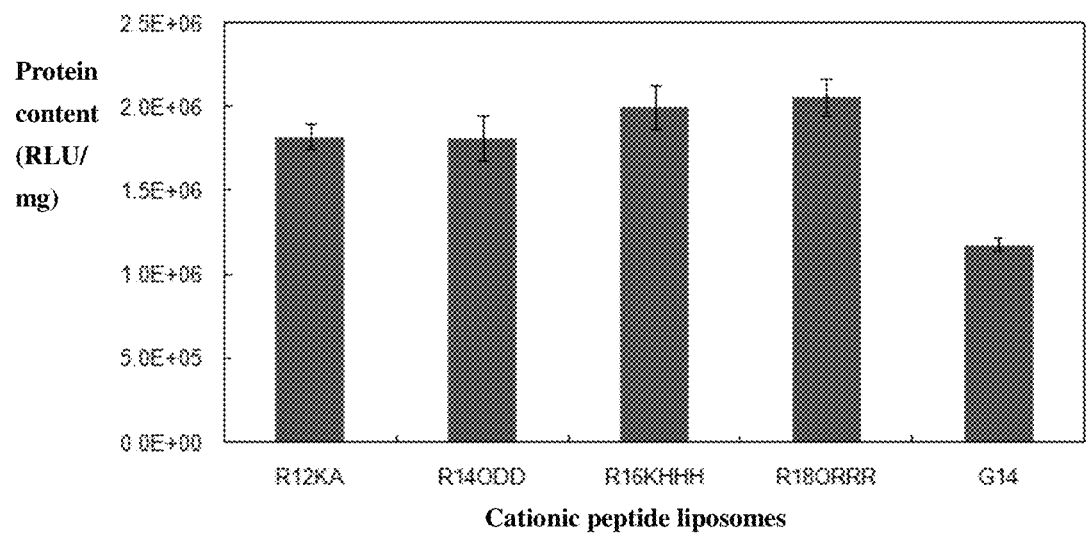
FIG. 6 is a luciferase expression diagram of carrying pGL-3 plasmid to transfect Hep-2 cells by using the cationic peptide liposomes detected by the microplate reader.

The experiment result is shown in the FIG. 6, wherein G14 is the Gemini liposome genetic vector, and preferably, a mass ratio of the liposome to DNA is 6:1. 4 liposomes can carry pGL3 plasmid to transfect NCI-H460 and Hep-2 cells. The transfection efficiency is the optimum when N/P is 3:1. Compared with the Gemini liposome genetic vector, the transfection efficiency is improved by 50%.

(3) RNA Interference Experiment

Cell plating is not subjected to counting. 2 mL of overgrowing A549 cells are added into each well of the 12-well plate, and cultured for 24 h, wherein cell density is about 50% to 60%. 200 μL of liposome/siRNA complex are added into each well, transfected for 18 h, and then, cultured in the growth culture medium for 30 h. The cells are washed with DPBS, adding 600 μL of lysate into each well, transferred to the 96-well whitplate after 20 min, 20 μL is added into each well, 80 μL of Promega E151A detection solution is added, and the relative enzyme activity is detected by using the multifunctional microplate reader (BioTek). 5 μL of lysate is added into the 96-well transparent plate, and total protein content via control is measured based on the Pierce BCA Protein Assay kit of the Thermoelectricity Corporation.

Figure 7:
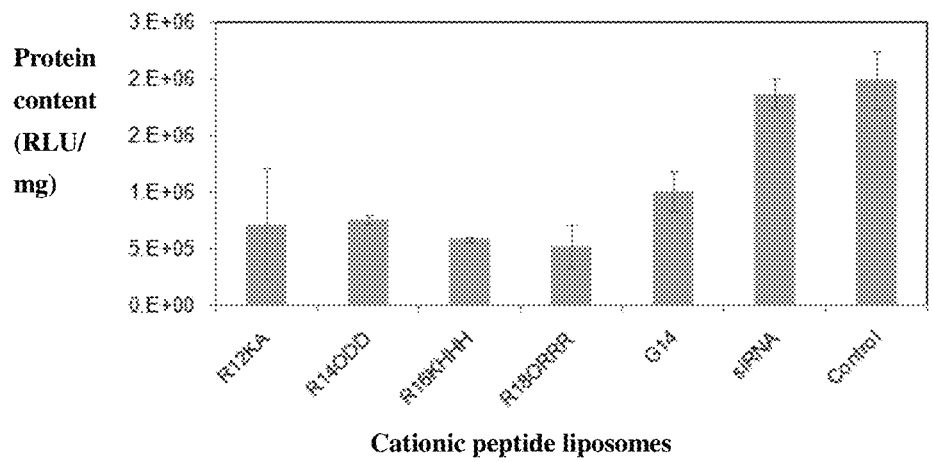
FIG. 7 is a luciferase gene-silencing diagram of carrying siRNA to transfect A549 cells by the cationic peptide liposomes detected by the microplate reader.

In the FIG. 7, the optimum N/P ratio of the liposome to siRNA is 6:1, and mediated RNAi studies to investigate the ability of 4 cationic liposomes carrying siRNA to transfect A549 cell silencing luciferase gene. G14 is the Gemini liposome gene vector, and siRNA and Control are blank reference. The result indicates that after transfection, the expression levels of luciferase genes are limited in different degrees. When the liposomes $R_{16}$KHHH/siRNA and $R_{18}$ORRR/siRNA are compared with the blank group, the silencing efficiency of luciferase genes can be up to 75%, and compared with the Gemini liposome, the silencing efficiency is improved by about 20%. It indicates that after the liposome-mediated siRNA entering into cells, it can form nucleic acid-protein complex (RNA-induced silencing complex, RISC) with protein in cytoplasm. Under the effect of RISC, siRNA specifically recognizes target mRNA, and cut the target mRNA under the effect of endonuclease, after being degraded under the effect of exonuclease, mRNA fragments cannot direct to synthesize the corresponding protein, and thereby realize silencing luciferase genes.

(4) Study on Cytotoxicity (MTT Colorimetric Method)

The cytotoxicity test on the cationic liposomes with high transfection efficiency is carried out by MTT method, using the commercial gene transfection reagents Lipofectamine 2000 and DOTAP as reference. Hep-2 and NCI-H460 cells are planted in a 96-well cell culture plate, adding 100 μL of cell culture fluid with concentration of $1.0 \times 10^6$/well (containing double antibodies and serum) into each well, and incubate for 24 h, so that the cell density is up to 80% to 90% on the transfection date. The growth culture medium is removed, washed with 100 μL culture medium, and substituted with the equivalent (100 μL) culture medium. The liposome and the plasmid DNA are complexed in ratios of 1:1, 2:1, 3:1, 4:1, 6:1 and 8:1 to be added into the cell culture plate. After carrying out cell culture for 24 h, 20 μL of MTT (Sigma, 5 mg/mL) is added into each well, and incubated for culturing for 4 to 4.5 h. The culture solution is removed, and 150 μL of DMSO lysis cells are added.

The detection principle based on the MTT colorimetric method is that succinodehydrogenase in the living cell mitochondria can make exogenous MTT reduced to water insoluble bluish violet crystallized Formazan and deposited in the cells, however dead cells do not have such function; and Formazan in the cells can be dissolved by dimethyl sulfoxide (DMSO), and its light absorption value is measured at the wavelength of 570 nm by using the microplate reader, which can indirectly reflect the quantity of living cells. Hence, the light absorption value of the blank control (cells without transfection) is 100%, and the survival rate (%) of the cells after being transfected is calculated. The calculation formula is:

$$\text{Cell survival rate (\%)} = [A]_{sample} / [A]_{control} \times 100\%$$

$[A]_{sample}$ is the light absorption value of the test well, and $[A]_{control}$ is the light absorption value of the negative blank control well.

Figure 8:
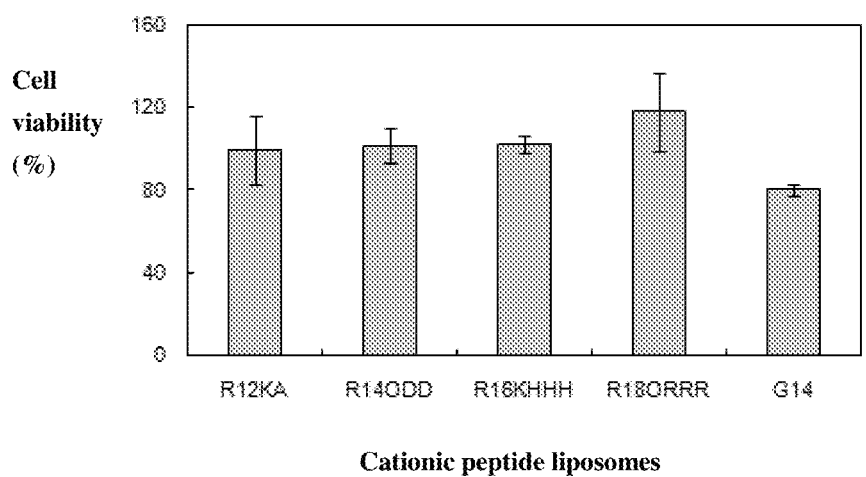
FIG. 8 is the detection of NCI-H460 cytotoxicity in the cell transfection process of detecting the cationic peptide liposome/gene complex of the invention using the MTT colorimetric method.
Figure 9:
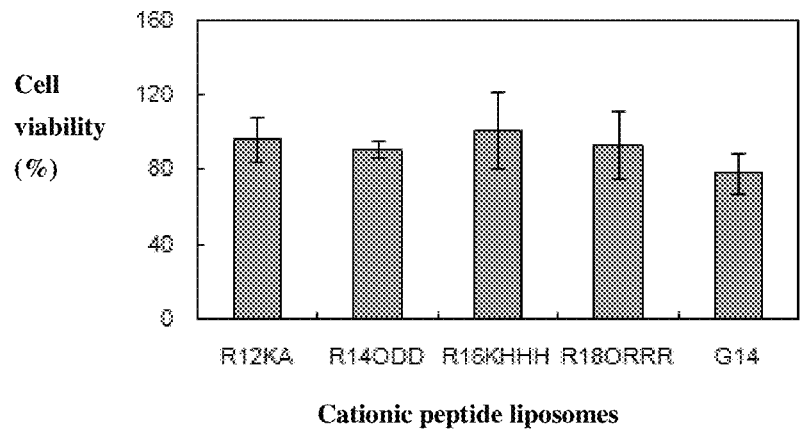
FIG. 9 is the measuring diagram of Hep-2 cytotoxicity in the cell transfection process of detecting the cationic peptide liposome/gene complex of the invention using the MTT colorimetric method.

The experiment result is shown in FIGS. 8 and 9, the horizontal coordinate is the prepared cationic peptide liposome, and a mass ratio of the preferable liposome to DNA is 6:1. FIG. 8 is using MTT colorimetric method, detecting NCI-H460 cytotoxicity of the cationic peptide liposome/gene complex of the invention in the cell transfection process. FIG. 9 is a measuring diagram of detecting Hep-2 cytotoxicity of the cationic peptide liposome/gene complex of the invention in the cell transfection process using MTT colorimetric method. 4 liposomes have little toxicity on NCI-H460 cells and Hep-2 cells, and cell survival rate is between 80% and 100%. Compared with the Gemini liposome genetic vector, the cell survival rate is improved by 20%.

(5) Study on Cell Intake

A549 cells are planted in a 6-well cell culture plate, 1 mL of cell culture solution with the concentration of $4.0\times10^6$/well (containing double antibodies and serum) is added into each well, and incubated for 24 h, so that the cell density is up to 70% to 80% on the transfection date.

The liposome and siRNA are complexed in a mass ratio of 3:1, total volume 200 μL is added into each hole, and cultured for 30 h.

Washing with DPBS, 0.3 mL of trypsin digestive cells are added into each well, and 0.8 mL culture medium is added after 1 to 2 min. After centrifuging, the cells are diluted with 0.4 mL DPBS, and analysis is carried out by using a flow cytometry.

Figure 10:
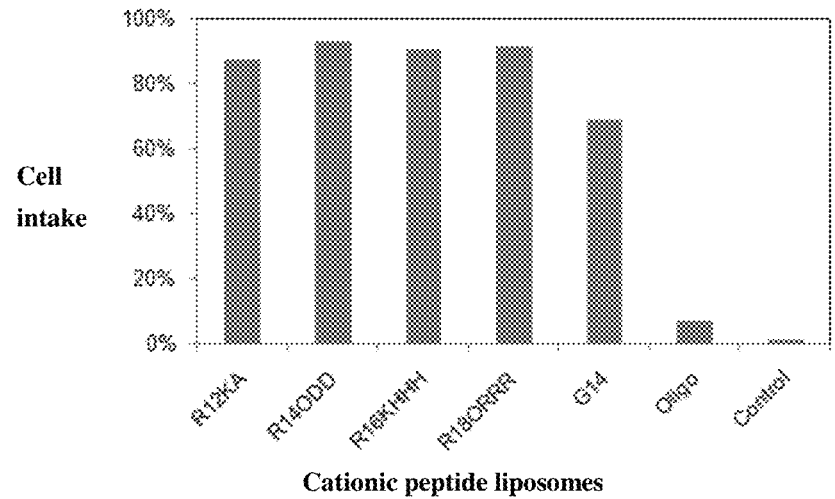
FIG. 10 is the cell intake diagram of the cationic peptide liposome/gene complex.

FIG. 10 is the detection result of cell intake, a mass ratio of the peptide liposome to siRNA is 6:1, G14 is the Gemini liposome genetic vector, and Oligo and Control are blank reference. 4 liposomes can enter into the cells, wherein the cell intake amount of the liposomes $R_{16}KHHH$ and $R_{18}ORRR$ is up to more than 90%, the cell intake amount of $R_{14}KDD$ is up to 80%, which are higher than that of the Gemini liposome genetic vector.

Embodiment 17 In-Vivo Biological Assessment Experiment (1) Establishment of Mouse Model Overgrowing A549 cells are extract, using DPBS wash it, 3 mL of Trypsin-EDTA is added, placed for 3 to 4 min, 5 mL of PRMI1640 containing serum and double antibodies is added, slightly blowing, transferring to the 15 mL centrifugal tube, and centrifuged at 1200 rpm for 5 min. And supernatant is removed, diluted in 1.5 mL of PBS, transplant below the skin of each naked mouse by 100 μL, and put into practice until tumors grow to 60 to –70 mm³.

(2) Carrying siRNA Silencing Luciferase Genes

The liposomes/siRNA is complexed in a mass ratio of 3:1, injected into tumor-bearing mice via caudal vein, tumors is took out after 24 h, placed in about 500 μL of lysate for 30 min, and centrifuged at temperature of 4° C. under 5000 rmp for 10 min.

The analytical method for the silencing effect is the same as step (3) in the embodiment 18.

The analytical method for the total protein content is the same as step (2) in the embodiment 18.

Figure 11:
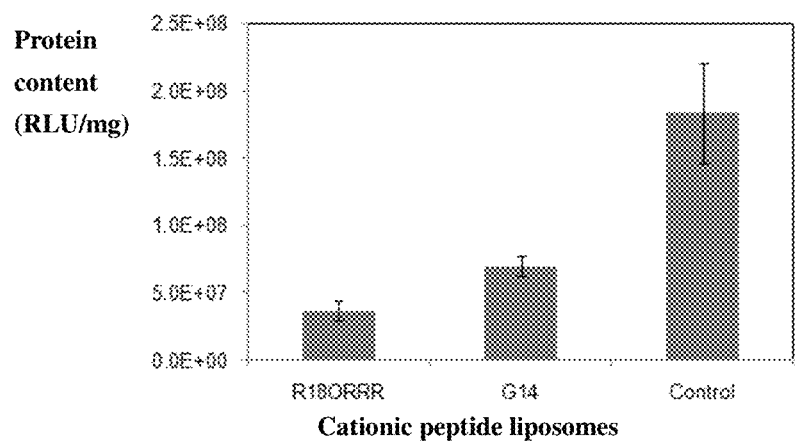
FIG. 11 is the diagram of carrying siRNA in-vivo silencing Luciferase gene by the cationic peptide liposome $R_{14}ODD$.

SiRNA is carried by the cationic liposome $R_{18}ORRR$, and the result of silencing luciferase genes in the tumor cells of the mice is shown as the FIG. 11, wherein Control is blank reference, G14 is the Gemini liposome genetic vector, and the mass ratio of the peptide liposome to siRNA is 6:1. After the liposome $R_{18}ORRR$ is injected, the expression of protein of luciferase genes in the mouse cells is obviously reduced, and compared with the blank control, the expression is reduced by about 2 times. In addition, the silencing efficiency is superior to that of the Gemini liposome genetic vector. It indicates that the cationic peptide lipid $R_{18}ORRR$ can lower the excessive expression of luciferase genes specifically and efficiently.

(3) Study on In-Vivo Cytotoxicity

The liposome/siRNA is complexed in a mass ratio of 3:1, injected into tumor-bearing mice via caudal vein, at intervals of two days, and injected for 5 times. Prior to administration, the weights of the mice are measured every day to observe the change in the weight growth of the mice in each group every day.

Figure 12:
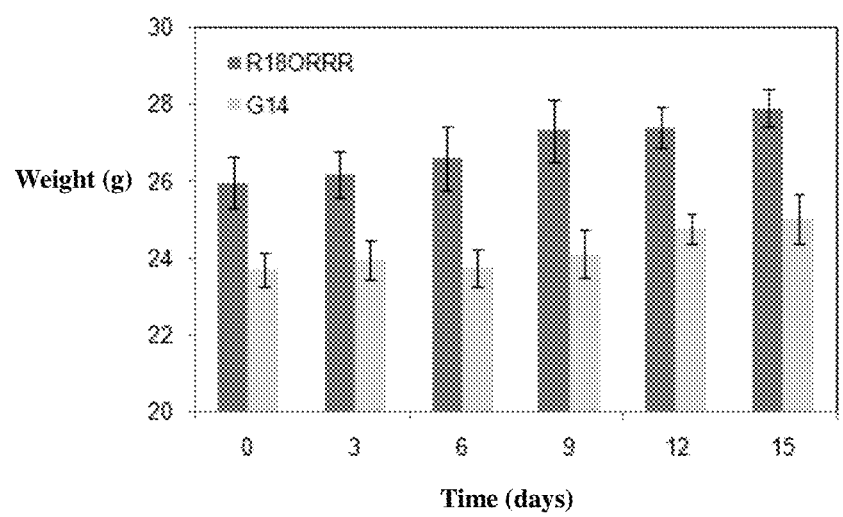
FIG. 12 is the weight change curve chart of mice with the in-vivo transfection of the cationic peptide liposome/gene complex.

As shown in the FIG. 12 for changes in the weights of the mice, the average weight of the mice is 25.9 g prior to the injection of the complex, the weights of the mice were in the obvious rising tread on the 6th day after the injection of the complex, with 27.89 g of average weight on the 15th day, and the weights were increased by 7.6%, indicating that the mice adapted to a certain dose of liposome $R_{18}ORRR$ and that the liposome did not affect the normal growth of the mice.

What is claimed is:

1. A bis-alkoxyl amide alkyl cationic peptide lipid comprising a chemical structure as below:

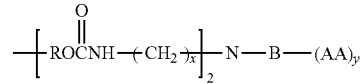

wherein, x is selected from 1 to 6; y is 1; R is selected from $C_{8-20}$ alkyl, and the alkyl comprises straight-chain alkyl and branched chain alkyl; AA is alanine (Ala); and B is Lys.

2. A synthetic method for the bis-alkoxyl amide alkylcationic lipid according to claim 1, wherein comprising the following steps of:

(1) carrying out acylation via an acylation reagent and an alcohol compound, wherein the acylation reagent is carbonyl diimidazole, and the alcohol compound is dodecanol, tetradecanol, hexadecanol or octadecanol, a molar ratio of the acylation reagent to the alcohol compound is 1:10 to 10:1, a reaction solvent is toluene, dichloromethane, DMF or chloroform, the reaction temperature is 10° C. to 60° C., and the reaction time is 0.5h to 12h;

(2) reacting the acylation product with a polyamine compound to prepare a dual long-carbon chain intermediate, the polyamine compound is polyamine selected from diethylenetriamine, dipropylenetriamine or dibutenetriamine, and a molar ratio of the polyamine to the acylation product is 1:2 to 1:8; a catalyst is triethylamine, sodium carbonate or methylpyridine, and an addition amount of the catalyst is 10% of a feeding quantity of the polyamine; reacting at temperatures of 10° C. to 100° C. for 2h to 48h; and recrystallizing to obtain an intermediate with a dual long-carbon chain: N,N-bis-alkoxyl amide alkylamine, wherein the recrystallizing solvent is ethyl acetate, or anhydrous ethyl alcohol/water mixed solvent (v/v=5:1);

(3) protecting the amino of amino acid by using a protective reagent to prepare a peptide head intermediate; wherein the amino acid is Lys; the protective reagent is di-tert-butyl dicarbonate ($Boc_2O$), Fmoc N-hydroxysuccinimideeste (Fmoc-OSu) or benzyl chloroformate (CbzCl); a molar ratio of the protective reagent to the amino acid is 1:8 to 8:1; a reaction solvent is 30 mL to 300 mL of water, acetonitrile or acetone, the reaction temperature is 0° C. to 25° C., and the reaction time is 0.5h to 2h; and recrystallizing to obtain the peptide head intermediate, wherein the recrystallizing solvent is ethyl acetate/petroleum ether mixed solvent (v/v=3:1);

(4) linking the peptide head intermediate prepared in step (3) with the dual long-carbon chain intermediate prepared in step (2) via amidation;

(a) activating the peptide head intermediate at temperatures of 0° C. to 30° C. for 0.5h to 2h to generate an active ester, wherein an activating reagent is 2-(7-azabenzotriazole)-N,N,N',N'-tetramethylureahexafluorophosphate ester (HATU), N,N'-dicyclohexylcarbimide (DCC) or HOBt, a molar ratio of amino acid to the activating reagent is 1:1 to 1:8, and a reaction solvent is dichloromethane, DMF or trichloromethane;

(b) adding dichloromethane, DMF or trichloromethane solution of the dual long-carbon chain intermediate into the reactant solution in step a, carrying out amidation to generate an amido bond by reacting the amino of the intermediate and the carboxyl of the peptide head intermediate, wherein a molar ratio thereof is 1:8 to 8:1, a catalyst is 4-dimethylamino pyridine (DMAP), or 1-hydroxybenzotriazole (HOBt), a molar ratio of the addition amount of the catalyst and the dual long-carbon chain intermediate is 1:1 to 1:8, the reaction time is 2h to 120h, and the reaction temperature ranges from 20° C. to 60° C.;

(5) removing the amino protecting reagent, wherein the deprotection reagent is trifluoroacetic acid or 10% NaHCO$_3$, a molar ratio of the deprotection reagent to the lipid compound is 1:1 to 1:2, the deprotection time is 0.5h to 12h, and the deprotection temperature ranges from 0° C. to 4° C., and through recrystallizing to purify, wherein a recrystallizing solvent is acetonitrile, anhydrous ethyl alcohol, ultrapure water, ethyl acetate or petroleum ether;

(6) after recrystallizing, dissolving the product in chloroform, purifying the crude product by using a silica column, and eluting by using a methanol/chloroform (a volume ratio of 3:1) mixed reagent, and removing the solvent via rotary evaporation at temperature of 70° C., and freeze-drying to obtain a bis-alkoxyl amide alkyl cationic peptide lipid compound containing one amino acid head; and (7) synthesizing the bis-alkoxyl amide alkyl cationic peptide lipid by taking a bis-alkoxyl amide alkyl cationic peptide lipid compound containing one amino acid head as a raw material: the peptide head intermediate prepared in step (3) with the cationic peptide lipid containing one amino acid head prepared in step (6), carrying out amino acid activation and amidation to obtain a cationic lipid compound with amino acid heads, a molar ratio thereof is 1:8 to 8:1, and the specific reactant condition and the purification method are the same as those in steps (4), (5) and (6).

3. A cationic peptide liposome prepared from the bis-alkoxyl amide alkyl cationic peptide lipid according to claim 1, wherein the cationic peptide liposome is an uniform and stable liposome formed by dispersing the bis-alkoxyl amide alkyl cationic peptide lipid in a water phase, and has particle sizes of about 100 nm and positive charges on the surface.

4. A preparation method for the bis-alkoxyl amide alkyl cationic peptide liposome according to claim 3, wherein comprising the following steps of:

(1) dissolving the bis-alkoxyl amide alkyl cationic peptide lipid and an additive in chloroform or methanol in a molar ratio of 1:1 to 8:1, so that the concentration of the bis-alkoxyl amide alkyl cationic peptide lipid compound is 0.5 mg/mL to 3 mg/mL, the additive is dioleoylphosphatidyl ethanolamine (DOPE), dioleoylphosphatidylcho line (DOPC), cholesterol or sucrose ester;

(2) blowing the solution under nitrogen to form a uniform film, and drying under vacuum for 4h to 12h;

(3) hydrating with ethanol, water and phosphate buffer or a mixed solution thereof at temperatures of 10° C. to 80° C. for 1h to 10h, and carrying out sonication until the solution is clarified to obtain the bis-alkoxyl amide alkyl cationic peptide liposome with the concentration of 0.5 mg/mL to 3.0 mg/m L.

5. A cationic peptide liposome/gene complex prepared from the bis-alkoxyl amide alkyl cationic peptide liposome according to claim 3, wherein uniform and stable nano-particles are dispersed in a water phase formed by the bis-alkoxyl amide alkyl cationic peptide liposome according to claim 3 and plasmid DNA (pDNA) or small interfering RNA (siRNA), through an electrostatic interaction.

6. A preparation method for the bis-alkoxyl amide alkyl cationic peptide liposome/gene complex according to claim 5, comprising the following steps of:

(1) dispersing the bis-alkoxyl amide alkyl cationic peptide liposome according to claim 3 in a cell culture solution, and mixing uniformly, so that a concentration ranges from 0.02 μg/μL to 0.16 μg/μL;

(2) diluting 0.5 μg to 1.0 μg of pDNA or siRNA in the cell culture solution, and mixing uniformly, so that a concentration of the plasmid is 0.02 μg/μL; and (3) mixing two diluted solutions in (1) and (2) uniformly in a mass ratio of liposome to gene of 1:1 to 8:1, placing at room temperature for 10 min to 40 min, and obtaining the bis-alkoxyl amide alkyl cationic peptide liposome/gene complex.

7. A bis-alkoxyl amide alkyl cationic peptide liposome/gene complex according to claim 5, wherein the gene complex is used for cell transfection and used for transfection in vivo.

* * * * *